(12) United States Patent
Kaji

(10) Patent No.: US 7,001,331 B2
(45) Date of Patent: Feb. 21, 2006

(54) ENDOSCOPE APPARATUS

(75) Inventor: Kunihide Kaji, Hachioji (JP)

(73) Assignee: Olympus Corporation, Tokyo (JP)

( * ) Notice: Subject to any disclaimer, the term of this patent is extended or adjusted under 35 U.S.C. 154(b) by 396 days.

(21) Appl. No.: 10/371,497

(22) Filed: Feb. 20, 2003

(65) Prior Publication Data
US 2003/0163025 A1 Aug. 28, 2003

(30) Foreign Application Priority Data
Feb. 25, 2002 (JP) ......................... 2002-048313

(51) Int. Cl.
*A61B 1/00* (2006.01)

(52) U.S. Cl. ............... 600/132; 600/178; 600/182; 600/153; 600/159; 362/580

(58) Field of Classification Search ........... 600/132, 600/153, 155–159, 178, 182; 606/46; 362/572, 362/574, 580
See application file for complete search history.

(56) References Cited

U.S. PATENT DOCUMENTS

| 4,325,606 A | | 4/1982 | Ikuno et al. |
| 4,572,164 A | * | 2/1986 | Yoshida et al. ............. 600/178 |
| 5,074,861 A | * | 12/1991 | Schneider et al. ............ 606/17 |
| 5,076,660 A | | 12/1991 | Messinger |
| 5,299,561 A | * | 4/1994 | Yoshimoto .................. 600/159 |
| 5,588,950 A | * | 12/1996 | Sano et al. ................. 600/178 |
| 5,865,727 A | | 2/1999 | Sano et al. |
| 6,033,360 A | | 3/2000 | Sano et al. |

FOREIGN PATENT DOCUMENTS

| GB | 1 393 699 | 5/1975 |
| JP | 9-51869 | 2/1997 |
| JP | 9-56672 | 3/1997 |
| JP | 10-127576 | 5/1998 |
| JP | 11-206707 | 8/1999 |
| JP | 2000-121960 | 4/2000 |

* cited by examiner

*Primary Examiner*—Linda C. M. Dvorak
*Assistant Examiner*—Matthew J Kasztejna
(74) *Attorney, Agent, or Firm*—Scully, Scott, Murphy & Presser

(57) ABSTRACT

A space through which a cooling fluid flows is provided in the inside of a connection portion between an endoscope and a light source device in order to cool heat generated in the connection portion. For example, a device for performing air supply or air suction (at least either one of air supply and air suction) in the endoscope communicates with the space, and cooling is effected by the flow of air formed by the device. In a preferred example of a cooling method, when neither air supply nor air suction is needed during manipulation of the endoscope, the device and the space are connected to each other to effect cooling, and when air supply or air suction is needed, the flow of air used for cooling is intercepted, and is exclusively directed to an air channel in the endoscope.

28 Claims, 7 Drawing Sheets

C-C'

ENDOSCOPE APPARATUS

CROSS-REFERENCE TO RELATED APPLICATION

This application is based upon and claims the benefit of priority from prior Japanese Patent Application No. 2002-048313, filed Feb. 25, 2002, the entire contents of which is incorporated herein by reference.

BACKGROUND OF THE INVENTION

1. Field of the Invention

The present invention relates to cooling heat generated in a connection portion through which illuminating light enters an endoscope when the illuminating light from an external light source is guided into the endoscope.

2. Description of the Related Art

In the case of endoscopes which are widely used in medical fields and industrial fields, target areas to be diagnosed or observed are in the insides of living bodies, plants and the like. For this reason, the target areas to be observed need to be illuminated. A general endoscope apparatus is provided with a light source device as an accessory device for an endoscope, and is constructed to guide illuminating light irradiated from an illuminating lamp inside the light source device, to an illuminating guide fiber provided in the endoscope. This illuminating light exits from an illuminating window provided at the tip end of an inserting part of the endoscope, and illuminates an area to be observed.

An example of the light source device is a high-luminance light source device which includes a high-luminance illuminating lamp, a lighting driving circuit for lighting and controlling this illuminating lamp by means of commercial power, and a light guide cable for guiding illuminating light projected from the illuminating lamp.

In recent years, it has become popular to use a small-sized battery-driven light source device that powers an illuminating lamp by using a battery such as a dry battery.

Portable endoscopes have been widely used. A portable endoscope is constructed to allow the high-luminance light source device and the battery-driven light source device to be removably connected to the endoscope, and is easily portably constructed so that endoscopic observation can be performed by using the battery-driven light source device even in the case where commercial power is difficult to use.

In the case where such a light source device (high-luminance light source device, battery-driven light source device, or other light source device) is connected to an endoscope and illuminating light from the light source device is guided into the endoscope, light losses occur as heat in a connection portion between the light source device and a manipulating part of the endoscope. Particularly in the case where the amount of illuminating light is large as in the high-luminance light source device, the vicinity of the connecting portion for connecting the light source device to the endoscope (light source connecting portion) is heated and becomes hot. Even if the heated portion is formed of a heat resistant member, it is difficult for a user to manipulate the endoscope without touching the heated portion. In the case of the battery-driven light source device as well, when a larger amount of illuminating light is to be obtained, the lighting driving power of the illuminating lamp needs to be made higher, so that a temperature rise occurs in the light source connecting portion.

In addition, in the case where the distance between the illuminating lamp and the light source connecting portion is short as in the battery-driven light source device, the heat radiation of the illuminating lamp becomes insufficient owing to a temperature rise of the light source connecting portion, which may also decrease the life of the illuminating lamp. Furthermore, in the case where the illuminating lamp burns out during the use of the endoscope, there may be a case where lamp replacing work is difficult to perform quickly, owing to the influence of a temperature rise of the light source connecting portion.

Several measures to cope with the generation of heat due to light losses in the light source connecting portion in the manipulating part of the endoscope are disclosed in JP-A-2000-121960. A first embodiment of JP-A-2000-121960 proposes the shape of a light source connecting portion which a user cannot easily touch during manipulation of the endoscope. A second embodiment proposes that a small hole be formed in a connecting portion to which an air supply tube is to be connected, so that air expelled through this small hole is applied to the light source connecting portion from the outside to cool the light source connecting portion.

BRIEF SUMMARY OF THE INVENTION

An endoscope apparatus according to the invention includes an inserting part having in its inside a light guide passage for illuminating light and constructed to be inserted into a target to be observed, a manipulating part positioned on a proximal-end side of the inserting part, and a light source connecting portion (a portion to which a light source is to be connected) positioned in the manipulating part and constructed to connect (or couple) the light guide passage to an external light source, the light source connecting portion having in its side a space through which a cooling fluid flows. The cooling fluid is, for example, air, water or oxygen. In the case of air, supplying air from an air supply or withdrawing air through suction can be used. In the case of water, water to be supplied through the inside of the endoscope can be used. In the case of oxygen, oxygen for use in treatment can be used.

Namely, a space through which the cooling fluid flows is provided in a connection portion between a light guide passage inside the endoscope and the external light source in order to cool heat generated owing to light losses in the connection portion. Accordingly, efficient cooling can be realized. Incidentally, the space through which the cooling fluid flows may also be readily formed in the light source connecting portion before connection or in a socket of the external light source to be connected to the light source connecting portion. However, this space may also be formed by the connection between the light source connecting portion in the manipulating part of the endoscope and the socket connected to the light source.

The manipulating part is a general term for parts and portions that are disposed on a more proximal side than the inserting part of the endoscope body (parts and portion not to be inserted into a target to be observed, and touched by the user during a manipulation). In the case where the endoscope is a flexible scope, the manipulating part in many cases is provided with a lever for bending the tip portion of the inserting part. In the case where the endoscope is a rigid scope, the manipulating part is a part to be gripped by a user for the purpose of manipulating the rigid scope during operation.

Preferably, the flow of air for causing air supply or air suction in the endoscope is guided into the space. In many cases, the inserting part of the endoscope has a channel for air supply and air suction. This channel is used exclusively for air supply or exclusively for air suction, but in many cases, the channel is used for both air supply and air suction. In the case of a channel used exclusively for air supply, the channel is called an air supply channel; in the case of a channel used exclusively for air suction, the channel is called an air suction channel; and in the case of a channel used for both air supply and air suction, the cannel is called an air supply and suction channel. All types of these channels are collectively called herein as an air channel. An air supply or air suction pipe of an external air driving device (an air supply source or an air suction source, typically, a compressor) which drives air to circulate through the air channel is preferably constructed to communicate with the above-described space from somewhere between the external air driving device and the air channel. According to this construction, it is not necessary to add a special device for driving the cooling fluid.

For example, when neither air supply nor air suction is performed in the endoscope, the passage through which air flows for air supply or air suction may be switched from the air channel in the endoscope to a passage including the above-described space. Only when air supply or air suction is to be performed in the endoscope, the flow of air is switched from the passage including the space to the air channel inside the endoscope. The proportion of the period of time for which air supply or air suction is performed is small in the entire period of manipulation time of the endoscope, so that even if the power of the external air driving device for air supply or air suction is used in a time-division manner, sufficient cooling can be achieved.

In the case where water is used as the cooling fluid, it is preferable that a water supply passage be arranged to pass through the space. In the case where oxygen is used as the cooling fluid, it is preferable that an oxygen supply passage be arranged to pass through the space.

In addition, the effect of cooling can be increased by contriving the shape of a member inside the space. For example, by providing a fin having a heat radiating function in the space, it is possible to increase the efficiency of heat transfer. By contriving the shape of the fin, it is also possible to improve the flowing direction of the cooling fluid and increase the efficiency of heat transfer to a further extent. For example, a helical fin may be disposed in the space to cause the cooling fluid to flow helically.

In addition, by adopting a construction in which the cooling fluid flows into the space through a plurality of inlet ports and flows out of the space through a plurality of outlet ports, it is possible to improve the flowing direction of the cooling fluid and increase the efficiency of heat transfer. Furthermore, by adopting a construction in which the cooling fluid flows into and out of the space in oblique directions, it is possible to produce a rotary flow and increase the efficiency of heat transfer.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Preferred embodiments of the present invention will be described hereinafter with reference to the drawings.

Figure 1A:
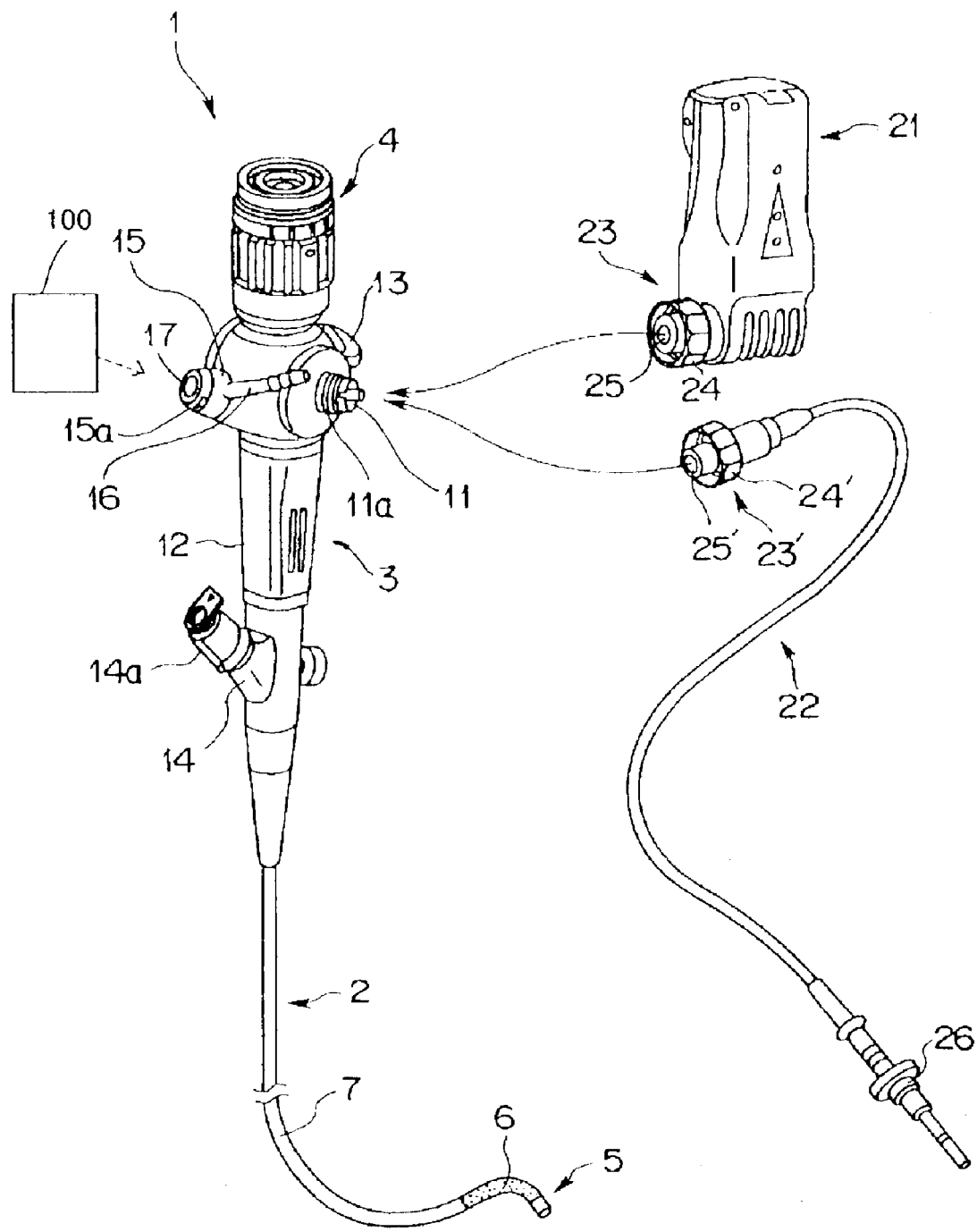
FIG. 1A is an isometric view showing an entire construction of an endoscope apparatus according to a preferred implementation of the present invention.

FIG. 1A is a view showing the entire construction of an endoscope apparatus according to a first embodiment. An endoscope 1 includes an inserting part 2 to be inserted into an area to be observed, a manipulating part 3 provided at the proximal end of the inserting part 2, and an ocular part 4 provided at the proximal end of the manipulating part 3.

Figure 1B:
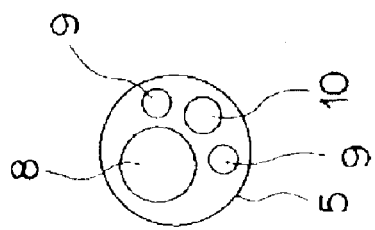
FIG. 1B is a view of a tip portion of the inserting part of the endoscope of FIG. 1A.

The inserting part 2 has a tip portion 5, a bendable portion 6 capable of being bent by manipulation from the manipulating part 3, and a flexible part 7 having flexibility, all of which are arranged in named order from a distal tip side of the inserting part 2. As shown in FIG. 1B, an air channel 8 (which, in each embodiment to be described below, is used for both air supply and air suction and is hereinafter called the air supply and suction channel 8) and an observing channel are disposed in the inside of the inserting part 2. The observing channel contains illuminating fiber cables for guiding illuminating light and an observing fiber cable. The end surface of the tip portion 5 is provided with the tip opening of the air supply and suction channel 8, illuminating lenses 9 provided at the respective illuminating fiber cables, and an objective lens 10 provided at the tip of the observing fiber cable.

The manipulating part 3 has an endoscope-side light source connecting portion 11 to which an external light source device is to be connected (or coupled), a grip 12 to be gripped by a user, an angle lever 13 for bending and manipulating the bendable portion 6 of the inserting part 2, a forceps inserting portion 14 having a forceps inserting port communicating with a forceps channel (not shown) provided in the inserting part 2, and an air connecting portion 15 connected to the air supply and suction channel 8 (in each embodiment to be described below, the air connecting portion 15 is a connecting portion to be used for both air supply and air, suction and is hereinafter called the air supply and suction connecting portion 15). Incidentally, the term "air connecting portion" means any of an air connecting portion for air supply only, an air connecting portion for air suction only, and an air connecting portion for both air supply and air suction.

The endoscope-side light source connecting portion 11 is provided with a threaded portion 11a onto which to screw a light source socket of the external light source device. The forceps inserting portion 14 is constructed so that the forceps inserting port is covered up by a forceps opening cover 14a when forceps need not be inserted into the inserting part, 2. The air supply and suction connecting portion 15 is provided with a tube fitting portion 16 to be connected to an air supply and suction device 100 which is an air driving device (an external air supply and suction source, for example, a compressor), and a switching button 17 for switching a portion with which the tube fitting portion 16 is to communicate, between the air supply and suction channel 8 and a cooling pipe which will be described later. Incidentally, the air supply and suction connecting portion 15 is generally provided with a leak portion 15a (such as a relief valve) for regulating pressure to prevent the air supply and suction pressure applied by the air supply and suction device 100 from becoming a predetermined value or more.

The proximal end of the observing fiber cable, which is inserted to extend from the tip portion 5 of the inserting part 2 to the manipulating part 3, is disposed in the ocular part 4, and an ocular lens is disposed at the proximal end of the observing fiber cable.

When an observer is to manipulate the endoscope 1, the observer grips the grip 12 of the manipulating part 3 and inserts the inserting part 2 into an area to be observed, while bending and manipulating the bendable portion 6 of the inserting part 2 by using the angle lever 13 of the manipulating part 3. Then, the observer illuminates the area to be observed with illuminating light which enters from the endoscope-side light source connecting portion 11 and is guided to the illuminating fiber cables and emitted from the illuminating lenses 9 of the tip portion 5. An image of the area to be observed is picked up by the objective lens 10, and the observer observes the image through the observing fiber cable disposed to extend from the inserting part 2 to the manipulating part 3, as well as through the ocular lens of the ocular part 4.

During the observation of the area to be observed, if mucus or foreign matter adheres to the objective lens 10 or the illuminating lenses 9 of the tip portion 5 of the inserting part 2, the observer supplies or sucks air by using the air supply and suction device 100 fitted to the tube fitting portion 16 of the air supply and suction connecting portion 15 of the manipulating part 3, thereby removing or sucking the mucus or the foreign matter.

When the mucus or the foreign matter adhering to the tip portion 5 of the inserting part 2 is to be removed through air supply or air suction, it is necessary to avoid supplying or sucking unnecessary air. The reason for this is that, for example in the case of a medical endoscope, since an organ which is an area to be observed in a body cavity has a definite volume, it is not preferable to supply or suck air to or from such an organ to an extent greater than necessary. For this reason, it is customary to complete manipulation for air supply and air suction in a short time with respect to the entire period of observation time. Accordingly, the period of time for which manipulation for air supply or air suction is not being performed is long in the entire period of observation time, and therefore, the endoscope 1 is constructed to allow air supply or suction pressure to escape through the leak portion 15a provided in the air supply and suction connecting portion 15, so that the air supply or suction pressure is prevented from becoming greater than necessary during that period of time.

Examples of the external light source device to be connected to the endoscope-side light source connecting portion 11 of the manipulating part 3 are a battery light source 21 which is a battery-driven light source and a high-luminance light source device (not shown, however, a light guide cable 22 for guiding high-luminance illuminating light from the high-luminance light source device is shown in FIG. 1).

The battery light source 21 integrally includes an illuminating lamp, a battery power source for driving the illuminating lamp to emit light, and a light source socket 23 to be directly fitted to the endoscope-side light source connecting portion 11 of the manipulating part 3. The light source socket 23 has a cap 24 with a threaded portion to be screwed onto the threaded portion 11a provided on the endoscope-side light source connecting portion 11, and a condenser lens 25 for condensing light emitted from the illuminating lamp.

The light guide cable 22 has, at one end, a light source socket 23' to be connected to the endoscope-side light source connecting portion 11 of the manipulating part 3, and the light source socket 23' has the same function as the light source socket 23 of the battery light source 21. The light guide cable 22 has at the other end an external light source connector 26 to be connected to the high-luminance light source device.

When the battery light source 21 is connected to the endoscope-side light source connecting portion 11 of the manipulating part 3, illuminating light emitted from the illuminating lamp driven by the battery power source of the battery light source 21 is irradiated onto the endoscope-side light source connecting portion 11 through the condenser lens 25. On the other hand, when the high-luminance light source device is connected to the endoscope-side light source connecting portion 11 of the manipulating part 3 through the light guide cable 22, illuminating light emitted from the high-luminance light source device is irradiated onto the endoscope-side light source connecting portion 11 from the condenser lens 25' of the light source socket 23' through the light guide cable 22.

When illuminating light is irradiated onto the endoscope-side light source connecting portion 11 of the manipulating part 3 with the battery light source 21 or the light guide cable 22 connected to the endoscope-side light source connecting portion 11 in the above-described manner, heat is generated by light losses in the portion of connection between the endoscope-side light source connecting portion 11 and the light source socket 23 or light source socket 23'. Even if each of the endoscope-side light source connecting portion 11 and the light source sockets 23 and 23' is formed of a member superior in heat resistance, the user may touch a heat generating portion or surrounding heated portion while manipulating the endoscope 1 with the manipulating part 3, and may suffer inferior manipulability.

A mechanism which positively radiates heat generated at the endoscope-side light source connecting portion 11 and' prevents the manipulability of the endoscope 1 from being impaired when the user touches the heat generating portion will be described below with reference to FIGS. 2A to 4B.

First, a basic concept of the first embodiment will be described below with reference to FIG. 2A. Incidentally, in FIG. 2A, the same reference numerals are used to denote the same parts and portions as those shown in FIG. 1.

Figure 2B:
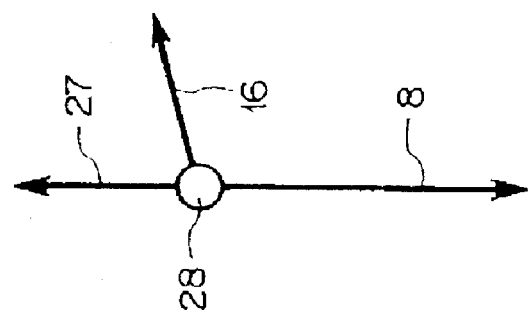
FIG. 2B is an explanatory view aiding in explaining the function of an air supply/air suction switching button of the manipulating part of the endoscope of FIG. 1A.
Figure 2A:
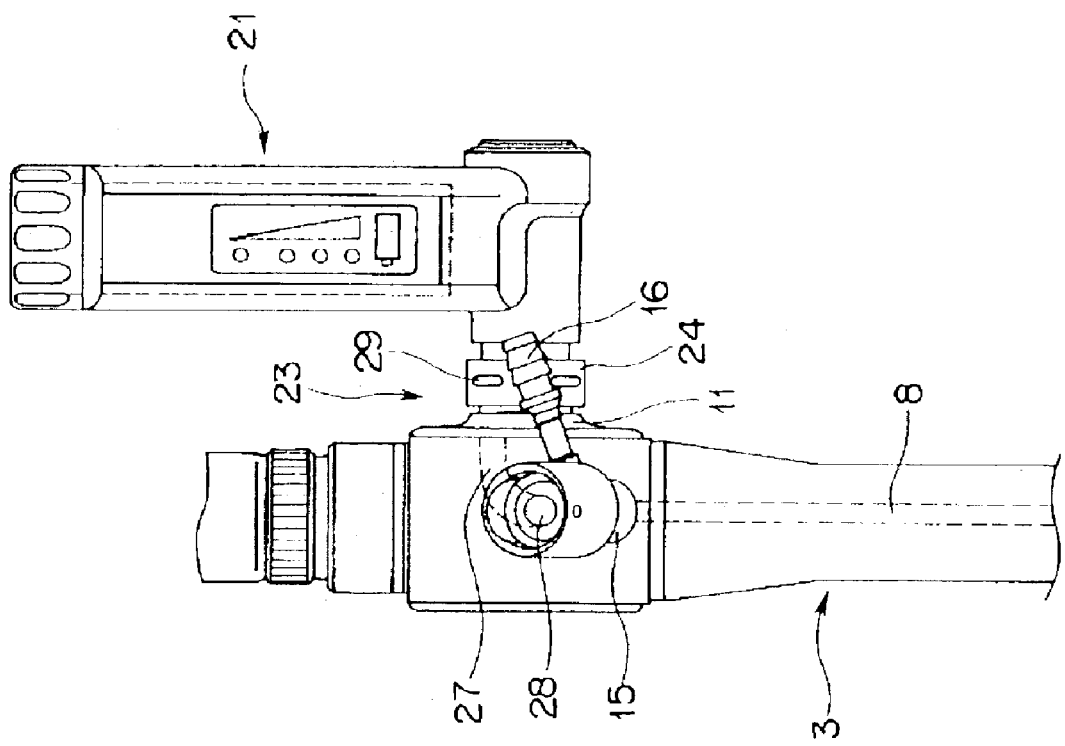
FIG. 2A is a plan view showing the relationship between a manipulating part of the endoscope apparatus according to the invention and a battery-driven light source, and showing the state of connection between the manipulating part of the endoscope and the battery-driven light source.

FIG. 2A shows the state in which the battery light source 21 is connected to the endoscope-side light source connecting portion 11 of the manipulating part 3 of the endoscope 1. In FIG. 2A, the illustration of the switching button 17 provided in the air supply and suction connecting portion 15 is omitted.

Connected to the air supply and suction connecting portion 15 are the tube fitting portion 16 to which a tube connected to the air supply and suction device 100 is fitted, the air supply and suction channel 8 which extends to the tip of the endoscope 1, and a cooling pipe 27 which is a tube through which to introduce air for cooling the heat generating portion. The tube fitting portion 16 has a tubular shape and serves as an air introducing tube.

A cooling pipe inlet 28 is provided in an upper portion of the air supply and suction connecting portion 15, and a space which follows the cooling pipe inlet 28 communicates with the tube fitting portion 16, the air supply and suction channel 8 and the internal passage of the cooling pipe 27.

The switching button 17 is fitted in the cooling pipe inlet 28, a portion to or from which air is to be supplied or sucked by the air supply and suction device 100 fitted to the tube fitting portion 16 can be switched between the air supply and suction channel 8 and the cooling pipe 27 by the manipulation of the switching button 17.

The cooling pipe 27 is disposed to extend from the cooling pipe inlet 28 to the vicinity of the endoscope-side light source connecting portion 11, and communicates with cooling pipe openings 29 provided in the cap 24 of the light source socket 23 and in a cap 24' of the light source socket 23', each of which light source sockets 23 and 23' is to be screwed onto the endoscope-side light source connecting portion 11.

Specifically, as shown in FIG. 2B, the cooling pipe inlet 28 of the air supply and suction connecting portion 15 serves to bifurcate a passage through which air is to be supplied or sucked by the air supply and suction device 100 connected to the tube fitting portion 16, into the air supply and suction channel 8 and the cooling pipe 27. Namely, a communicating passage through which air is to be supplied or sucked via the tube fitting portion 16 is switched to either one of the air supply and suction channel 8 and the cooling pipe 27 by the switching button 17 fitted in the cooling pipe, inlet 28.

Figure 3A:
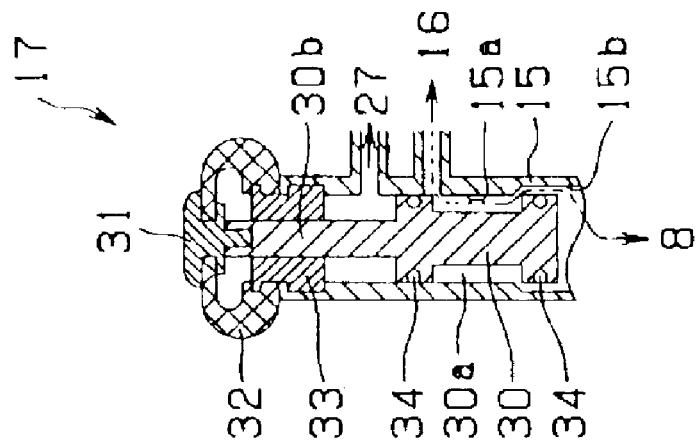
FIGS. 3A to 3C are cross-sectional views aiding in explaining the construction and the operation of the air supply/air suction switching button provided in an air supply and suction connecting portion of the endoscope of FIG. 1A.
Figure 3B:
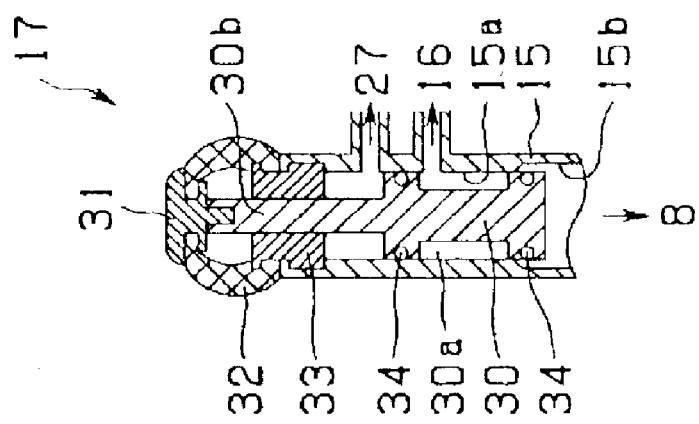
Figure 3C:
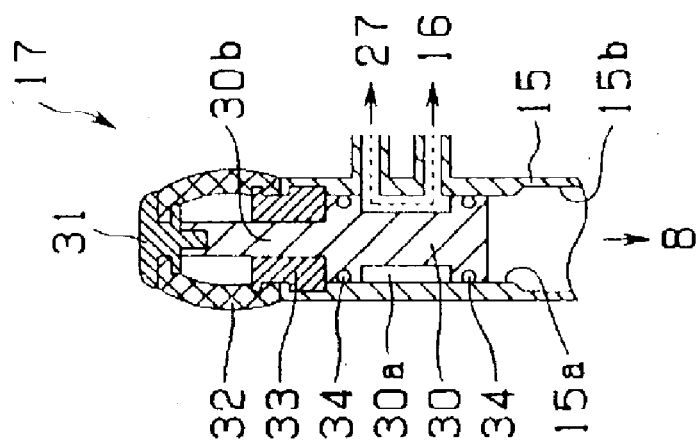

The construction of the switching button 17 disposed to be fitted in the cooling pipe inlet 28 of the air supply and suction connecting portion 15 will be described below with reference to FIGS. 3A to 3C. FIG. 3A shows the state in which the tube fitting portion 16 communicates with the cooling pipe 27, FIG. 3B shows the state in which the tube fitting portion 16 does not communicate with either of the cooling pipe 27 and the air supply and suction channel 8, and FIG. 3C shows the state in which the tube fitting portion 16 communicates with the air supply and suction channel 8.

The air supply and suction connecting portion 15 has an approximately cylindrical shape, and a small-diameter portion 15a having a small inner diameter is formed in the upper portion of the cylindrical shape, and a large-diameter portion 15b having a larger inner diameter than the small-diameter portion 15a is formed in a portion below the E small-diameter portion 15a. As viewed in FIGS. 3A to 3C, the proximal end of the tube fitting portion 16 communicates with the lower side of the small-diameter portion 15a, the proximal end of the cooling pipe 27 communicates with the upper side of the small-diameter portion 15a, and the proximal end of the air supply and suction channel 8 communicates with the large-diameter portion 15b.

A piston portion 30 of cylindrical shape is slidably fitted in the small-diameter portion 15a of the air supply and suction connecting portion 15. A concave portion 30a having a shape and size which enable the tube fitting portion 16 and the proximal end of the cooling pipe 27 to communicate with each other is formed in an approximately middle portion of the piston portion 30. O-rings 34 are respectively provided on surfaces of the piston portion 30 that are in sliding contact with the small-diameter portion 15a, at positions above and below the concave portion 30a of the piston portion 30. A shaft portion 30b which extends upwardly from the air supply and suction connecting portion 15 is provided on the top of the piston portion 30 as viewed in FIGS. 3A to 3C.

The shaft portion 30b is supported for sliding movement in the air supply and suction connecting portion 15 by a fixing portion 33 provided at the top of the air supply and suction connecting portion 15. In addition, a button portion 31 is provided at the head of the shaft portion 30b. An elastic portion 32 (formed of, for example, rubber) having an approximately cylindrical shape is fitted between the button, portion 31 and the fixing portion 33.

As shown in FIG. 3A, the piston portion 30 is constantly urged upwardly as viewed in FIG. 3A by a biasing force from the elastic portion 32. The concave portion 30a of the piston portion 30 is positioned so that the tube fitting portion 16 and the cooling pipe 27 communicate with each other. Accordingly, an air supply or suction force from the air supply and suction device 100 connected to the tube fitting portion 16 is guided from the tube fitting portion 16 to the cooling pipe 27 through the concave portion 30a of the piston portion 30.

FIG. 3B shows the state in which the button portion 31 is pressed downwardly as viewed in FIG. 3B from the position shown in FIG. 3A against the elasticity of the elastic portion 32. As shown in FIG. 3B, the concave portion 30a of the piston portion 30 is positioned to cover only the tube fitting portion 16. Accordingly, the communication between the tube fitting portion 16 and the cooling pipe 27 is released, and the tube fitting portion 16 is closed. In this state, an air supply or suction force from the air supply and suction device 100 is not transmitted to the cooling pipe 27 nor the air supply and suction channel 8.

FIG. 3C shows the state in which the button portion 31 is pressed further downwardly as viewed in FIG. 3C from the position shown in FIG. 3B. As shown in FIG. 3C, the bottom side of the concave portion 30a of the piston portion 30 is positioned in the large-diameter portion 15b of the air supply and suction connecting portion 15, and the tube fitting portion 16 and the air supply and suction channel 8 communicates with each other. Accordingly, an air supply or suction force from the air supply and suction device 100 connected to the tube fitting portion 16 is guided from the tube fitting portion 16 to the air supply and suction channel 8 through the concave portion 30a of the piston portion 30.

Namely, the inner circumferential surface of the air supply and suction connecting portion 15 has a cylindrical shape having different inside diameters, and the proximal end of the air supply and suction channel 8 is connected to one end of the large-diameter portion 15b of this cylindrical shape, and the proximal end of the tube fitting portion 16 and the proximal end of the cooling pipe 27 are disposed on the outer surface of the small-diameter portion 15a of the cylindrical shape. The piston portion 30 that is fitted in the small-diameter portion 15a of the cylindrical shape and has the concave portion 30a is made to move upwardly or downwardly in sliding contact with the air supply and suction connecting portion 15. Accordingly, an air supply or suction force from the air supply and suction device 100 connected to the tube fitting portion 16 can be selectively supplied to either of the cooling pipe 27 and the air supply and suction channel 8.

Incidentally, in the first embodiment, the tube fitting portion 16 and cooling pipe 27 provided in the air supply and suction connecting portion 15 are respectively disposed at different heights, and the piston portion 30 is disposed to be capable of moving upwardly or downwardly in sliding contact with the air supply and suction connecting portion 15. However, the switching structure is not limited to this example. The switching structure may have any other shape and construction that enable the air supply or suction force from the air supply and suction device 100 fitted to the tube fitting portion 16 to selectively communicate with the cooling pipe 27 and the air supply and suction channel 8.

In the first embodiment, the state in which the air supply and suction device 100 communicates with only the cooling pipe 27 and the state in which the air supply and suction device 100 communicates with only the air supply and suction channel 8 can be exclusively switched therebetween by the switching structure. However, when the air supply and suction device 100 and the air supply and suction channel 8 are in the state of communicating with each other, the air supply and suction device 100 and the cooling pipe 27 may also be made to communicate with each other. In this case, since the output of the air supply and suction device 100 is dispersed, the capacity of air supply and air suction through the air supply and suction channel 8 and the capacity to cool the heat generating portion through the cooling pipe 27 become small. However, since the air supply and suction device 100 having a sufficient capacity can be adopted, no problems occur in practical use, and since the heat generating portion and/or the surrounding heated portion are substantially constantly cooled through the cooling pipe 27, the possibility of overheating of the heat generating portion and/or the heated portion is low.

Figure 4A:
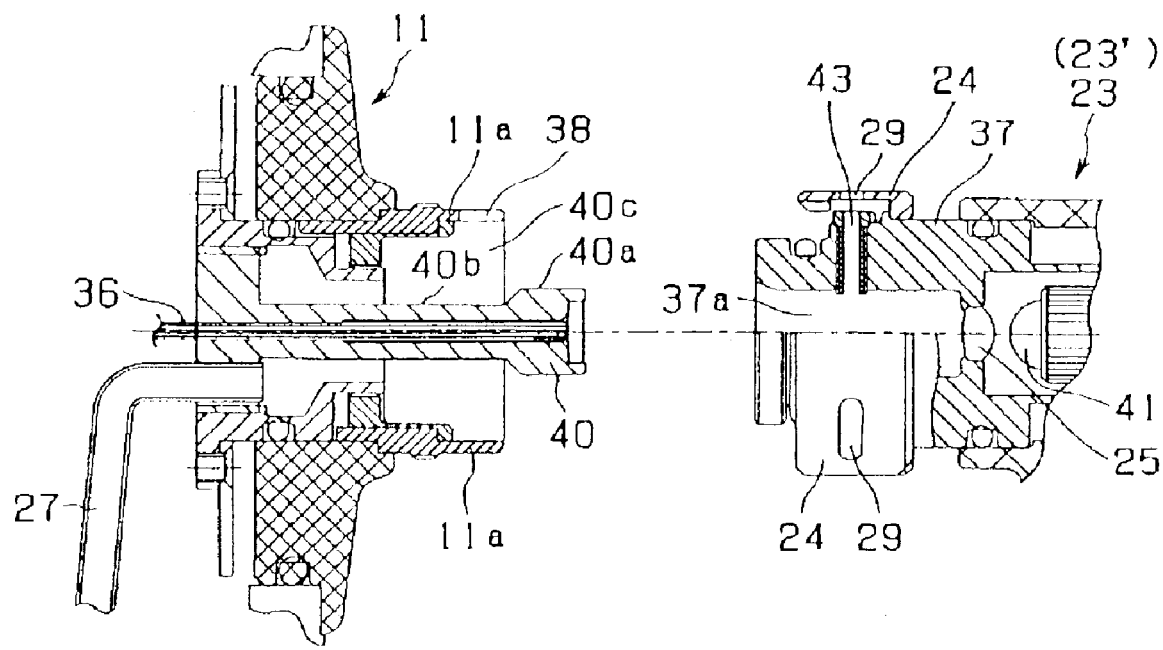
FIG. 4A is a cross-sectional view showing the construction of a light source connecting portion of the manipulating part and the construction of a light source fitting socket of an external light source in a first embodiment of the endoscope apparatus according to the present invention, and showing the state in which the light source connecting portion and the light source fitting socket are not connected to each other.
Figure 4B:
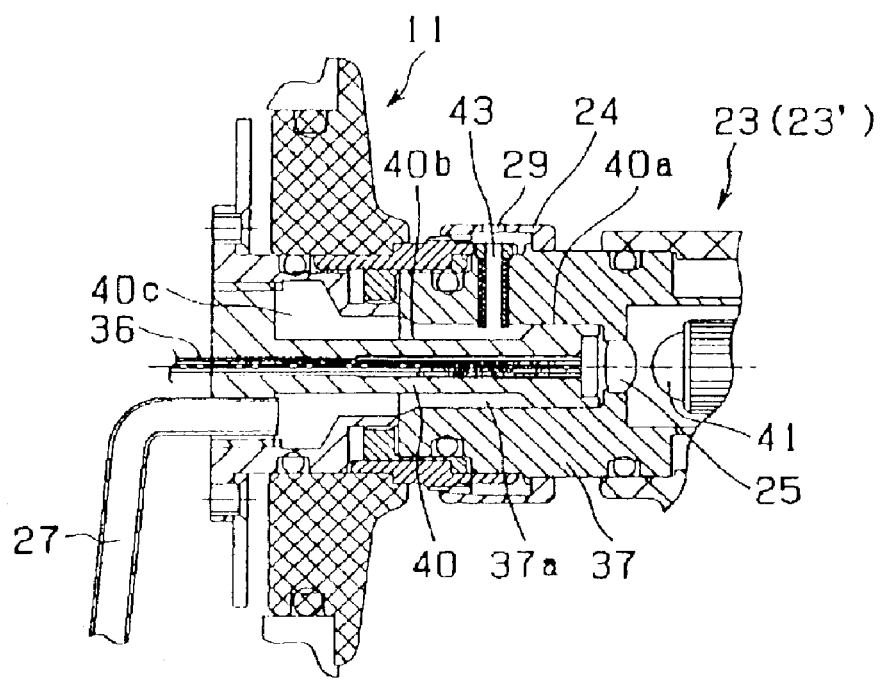
FIG. 4B is a cross-sectional view showing the state in which the light source connecting portion and the light source fitting socket shown in FIG. 4A are connected to each other.

In the following description using FIGS. 4A and 4B, reference will be made to the shape and the construction of the endoscope-side light source connecting portion 11 of the manipulating part 3 and the shape and the construction of the light source socket 23 of the battery light source 21 which is an external light source device as well as the shape and the construction of the light source socket 23' of the light guide cable 22 connected to an external light source device. In FIGS. 4A and 4B, the same reference numerals are used to denote the same parts and portions as those shown in FIGS. 1A–3C.

FIG. 4A shows the state in which the endoscope-side light source connecting portion 11 and the light source socket 23 or 23' are not connected to each other, whereas FIG. 4B shows the state in which the endoscope-side light source connecting portion 11 and the light source socket 23 or 23' are connected to each other. Since the light source socket 23 of the battery light source 21 and the light source socket 23' of the light guide cable 22 have the same shape and construction, the light source socket 23 of the battery light source 21 will be described below by way of example.

As shown in FIG. 4A, a fiber cable receiving member 40 which fixes the proximal end of an illuminating fiber cable 36 made of a bundle of a plurality of optical fibers is provided in the central portion of the endoscope-side light source connecting portion 11. The fiber cable receiving member 40 has an approximately cylindrical shape, and the proximal end of the illuminating fiber cable 36 is inserted and fixed in a hollow portion of the fiber cable receiving member 40. The outer circumferential portion of the fiber cable receiving member 40 has at its extending end a large-diameter portion 40a to which the condenser lens 25 of the light source socket 23 (to be described later) is opposed, and a small-diameter portion 40b formed to extend from the large-diameter portion 40a to the proximal end of the endoscope-side light source connecting portion 11.

The outer circumferential portion of the endoscope-side light source connecting portion 11 has the threaded portion 11a having an external thread onto which to screw the cap 24 (to be described later) of the light source socket 23. A space 40c is formed between the inner circumferential surface of the threaded portion 11a and the outer circumferential surface of the fiber cable receiving member 40.

The tip opening of the cooling pipe 27 is positioned in communication with the space 40c. A notch 38 that extends axially is provided in the threaded portion 11a at a predetermined position thereof. This notch 38 serves to restrict the relationship in connection position between the endoscope-side light source connecting portion 11 and the light source socket 23 when the light source socket 23 (to be described later) is screwed onto the threaded portion 11a. Namely, the tip opening of the cooling pipe 27 communicates with the space 40c and the notch 38 of the threaded portion 11a.

In the case where the battery light source 21 is adopted as an external light source device, the light source socket 23 fixes and holds an illuminating portion 41 that contains the illuminating lamp and the condenser lens 25 which condenses the illuminating light irradiated from the illuminating portion 41. However, in the case where a high-luminance light source device is adopted as an external light source device and the light guide cable 22 from the high-luminance light source device is connected to the endoscope-side light source connecting portion 11, not the illuminating lamp but the end surface of optical fibers passing through the light guide cable 22 is positioned in the illuminating portion 41. The light source socket 23 also has a guide member 37 which has an approximately cylindrical shape and a concave portion 37a into which to fit the fiber cable receiving member 40 of the endoscope-side light source connecting portion 11. The cap 24 has an internal thread screwed onto the external thread of the threaded portion 11a of the endoscope-side light source connecting portion 11 which is turnably provided on the outer circumference of the tip portion of the guide member 37. The cap 24 has the cooling pipe openings 29 formed by opening slits, which cause its inner and outer circumferences to communicate with each other. A cylindrical pin 43 (having a hollow passage in its inside) which allows the inner and outer circumferential sides of the concave portion 37a into which to fit the fiber cable receiving member 40 to communicate with each other is embedded in the guide member 37. The pin 43 is positioned under the inner circumferential surface of the cap 24. Incidentally, the condenser lens 25 is watertightly fixed to a predetermined position of the inner circumferential surface of the guide member 37, for example by adhesion with an adhesive having water resistance or chemical resistance or by subjecting the outer circumferential surface of the guide member 37 to metallization treatment followed by soldering with metal.

When the endoscope-side light source connecting portion 11 and the light source socket 23 are to be connected to each other, the extending end of the fiber cable receiving member 40 of the endoscope-side light source connecting portion 11 is inserted into the concave portion 37a of the light source socket 23 and, at the same time, the notch 38 of the threaded portion 11a of the endoscope-side light source connecting portion 11 is fitted onto the pin 43 of the light source socket 23, and the cap 24 is screwed onto the threaded portion 11a. Then, as shown in FIG. 4B, the extending end of the fiber cable receiving member 40 is positioned in front of the condenser lens 25. In this manner, the cooling pipe 27 is placed in the state of communicating with the air through the space 40c of the endoscope-side light source connecting portion 11 (as the result of this connection, the space 40c is extended to the space between the inner surface of the concave portion 37a and the outer surface of the fiber cable receiving member 40), the pin 43 of the light source socket 23 and the cooling pipe openings 29 of the pin 43.

Namely, when the air supply and suction device 100 is connected to the tube fitting portion 16 and the tube fitting portion 16 and the cooling pipe 27 are set to communicate with each other (as shown in FIG. 3A) by selection at the switching button 17, air supplied by the air supply and suction device 100 passes through the tube fitting portion 16, the cooling pipe 27, the space 40c surrounding the fiber cable receiving member 40 of the endoscope-side light source connecting portion 11, and the pin 43 of the light source socket 23, and flows out from the cooling pipe openings 29 of the cap 24.

In the meantime, the condenser lens 25 and the fiber cable receiving member 40 generate heat owing to the loss of illuminating light that occurs when illuminating light, emitted from the illuminating portion 41 of the light source socket 23 is condensed by the condenser lens 25 and is projected onto the fiber cable receiving member 40 of the endoscope-side light source connecting portion 11. The generated heat is transferred to the supplied air passing through the cooling pipe 27, the space 40c around the outer circumference of the fiber cable receiving member 40 of the endoscope-side light source connecting portion 11, and the pin 43, and flowing out from the cooling pipe openings 29 of the cap 24. Namely, when the air supplied by the air supply and suction device 100 is supplied to the cooling pipe 27 by selection at the switching button 17, the heat generated in the endoscope-side light source connecting portion 11 and the light source socket 23 of the battery light source 21 is transferred to the supplied air and vented to the atmosphere. Accordingly, the endoscope-side light source connecting portion 11 and the light source socket 23 of the battery light source 21 can be cooled to such an extent that the user is not precluded from manipulating the endoscope 1.

When air needs to be supplied to or sucked from the tip portion 5 of the inserting part 2 while the user is manipulating the endoscope 1, the user depresses the switching button 17 so that the tube fitting portion 16 connected to the air supply and suction device 100 and the air supply and suction channel 8 are set to communicate with each other, thereby enabling air to be supplied to or sucked from the tip portion 5. In addition, when the supply or suction of air to or from the tip portion 5 becomes unnecessary, the user releases the switching button 17, so that the switching button 17 is reset to its initial state by the elastic force of the elastic portion 32 and causes the tube fitting portion 16 to communicate with the cooling pipe 27, thereby restoring the operation of cooling the endoscope-side light source connecting portion 11 and the light source socket 23.

In addition, even when the air supply and suction device 100 is being driven in the state of being connected to the tube fitting portion 16, the pressure of air supply or air suction applied to the manipulating part 3 is released into the atmosphere together with the transfer of heat from the heat generating portion, so that the leak portion 15a of the air supply and suction connecting portion 15 may not need to be provided (the leak portion 15a may also be provided for pressure regulation).

Incidentally, during the air sucking operation of the air supply and suction device 100, when the tube fitting portion 16 and the cooling pipe 27 are set to communicate with each other by selection at the switching button 17, air is passed through the cooling pipe openings 29 of the light source socket 23, the pin 43, the space 40c surrounding the fiber cable receiving member 40, the cooling pipe 27 and the tube fitting portion 16, and is sucked into the air supply and suction device 100. The heat generating portion is cooled by this flow of air.

As is well known, the exterior of each of the endoscope 1 and the battery light source 21 is constructed as a watertight structure. Accordingly, during the cleaning of the endoscope 1, in the case where the endoscope 1 is dipped into a chemical or the like, even if the chemical or the like enters the concave portion 37a of the guide member 37 through the air supply and suction channel 8, the tube fitting portion 16 and the cooling pipe 27, the chemical or the like can be prevented from penetrating the interior of the manipulating part 3 of the endoscope 1 or the interior of the battery light source 21.

As described above, the endoscope apparatus according to the first embodiment has a bifurcated pipe having two branches, one of the branches is connected to the air supply and suction channel (air channel) 8 extended from the air supply and suction connecting portion (air connecting portion) 15 of the manipulating part 3 to the inserting part 2, and the other of the branches is connected to the cooling pipe 27 provided in the vicinity of the endoscope-side light source connecting portion 11. These bifurcated pipes can be switched therebetween by the switching button (switching mechanism) 17 so that it is possible to select the communication between the air supply and suction device (air driving device) 100 and the cooling pipe 27 or the communication between the air supply and suction device (air driving device) 100 and the air supply and suction channel 8. Accordingly, it is possible to easily switchably select the transfer of generated heat from the endoscope-side light source connecting portion 11 of the manipulating part 3 by means of the air supply and suction device (air driving device) 100 or the manipulation of supplying or sucking air to or from the tip portion 5 by means of the air supply and suction device 100. Except when air is being supplied to or sucked from the tip portion 5, the transfer of heat from the endoscope-side light source connecting portion 11 can be constantly effected, whereby the user can enjoy improved manipulability. Furthermore, it is possible to prevent a chemical or the like from penetrating the interior of the manipulating part 3 of the endoscope 1 or the interior of the battery light source 21.

Figure 5B:
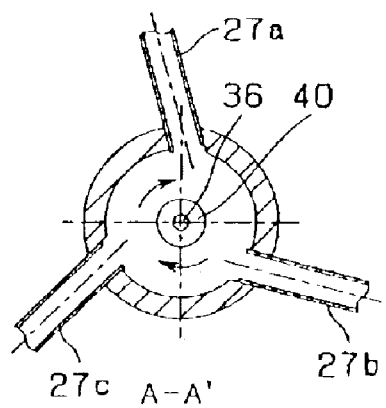
FIGS. 5A to 5C are cross-sectional views showing the construction of the light source connecting portion of the manipulating part and the construction of the light source fitting socket of the external light source in a second embodiment of the endoscope apparatus according to the present invention.
Figure 5A:
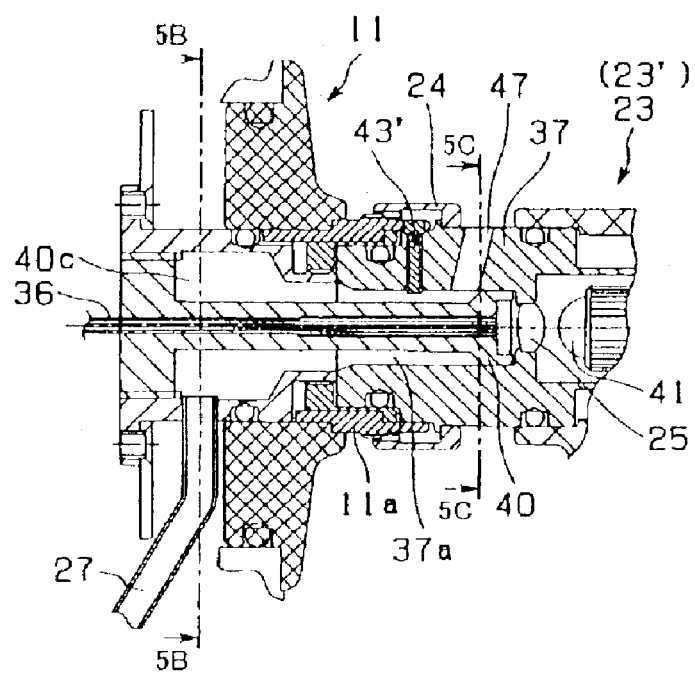
Figure 5C:
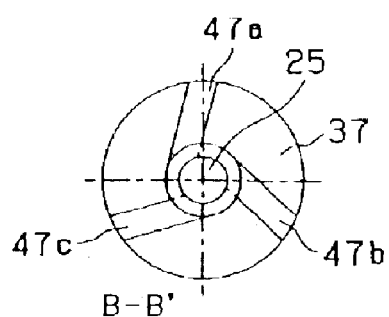

An endoscope apparatus according to a second embodiment of the invention will be described below with reference to FIGS. 5A to 5C. In the second embodiment, the endoscope-side light source connecting portion 11 and the light source socket 23 differ in construction from those of the first embodiment, and the following description refers to this point. FIG. 5A shows the state in which the endoscope-side light source connecting portion 11 and the light source socket 23 are connected to each other. In FIGS. 5A to 5C, the same reference numerals are used to denote the same parts and portions as those used in the first embodiment, and the detailed description of the same parts and portions is omitted.

In the second embodiment, as shown in FIG. 5B, the cooling pipe 27 extended to the vicinity of the endoscope-side light source connecting portion 11 is formed of a plurality of branch pipes, specifically, three branch cooling pipes 27a to 27c. The distal end of each of the three branch cooling pipes 27a to 27c communicates with the space 40c surrounding the fiber cable receiving member, 40 of the endoscope-side light source connecting portion 11 of the manipulating part 3. The cooling pipes 27a to 27c which communicate with the space 40c surrounding the fiber cable receiving member 40 are respectively secured at angles each slightly offset from the radial direction of the central axis of the fiber cable receiving member 40.

In the light source socket 23, as shown in FIG. 5A, the pin 43 provided in the guide member 37 is a cylinder (which does not contain a hollow passage), and exclusively serves to restrict the position of the light source socket 23 with respect to the notch 38 provided in the threaded portion 11a of the endoscope-side light source connecting portion 11. In addition, as shown in FIG. 5c, a plurality of communication holes 47a to 47c cause the concave portion 37a of the guide member 37 to communicate with the outside. The communication holes 47a to 47c are respectively disposed at angles each offset from the radial direction the central axis of the fiber cable receiving member 40 similarly to the cooling pipes 27a to 27c, and are respectively formed to extend in directions slightly inclined from directions perpendicular to the axis of the guide member 37. The cooling pipes 27a to 27c and the communication holes 47a to 47c are disposed to be offset from the radial direction of the central axis of the fiber cable receiving member 40 in mutually different directions.

In this construction, because the cooling pipes 27a to 27c and the communication holes 47a to 47c are offset, the air supplied from the cooling pipes 27a to 27c to the space 40c surrounding the fiber cable receiving member 40 of the endoscope-side light source connecting portion 11 forms a uniform air supply flow which swirls around the outer circumference of the fiber cable receiving member 40. Owing to this air supply flow, it is possible to realize a far higher cooling effect on heat generation at the fiber cable receiving member 40 and the light source socket 23.

Figure 6A:
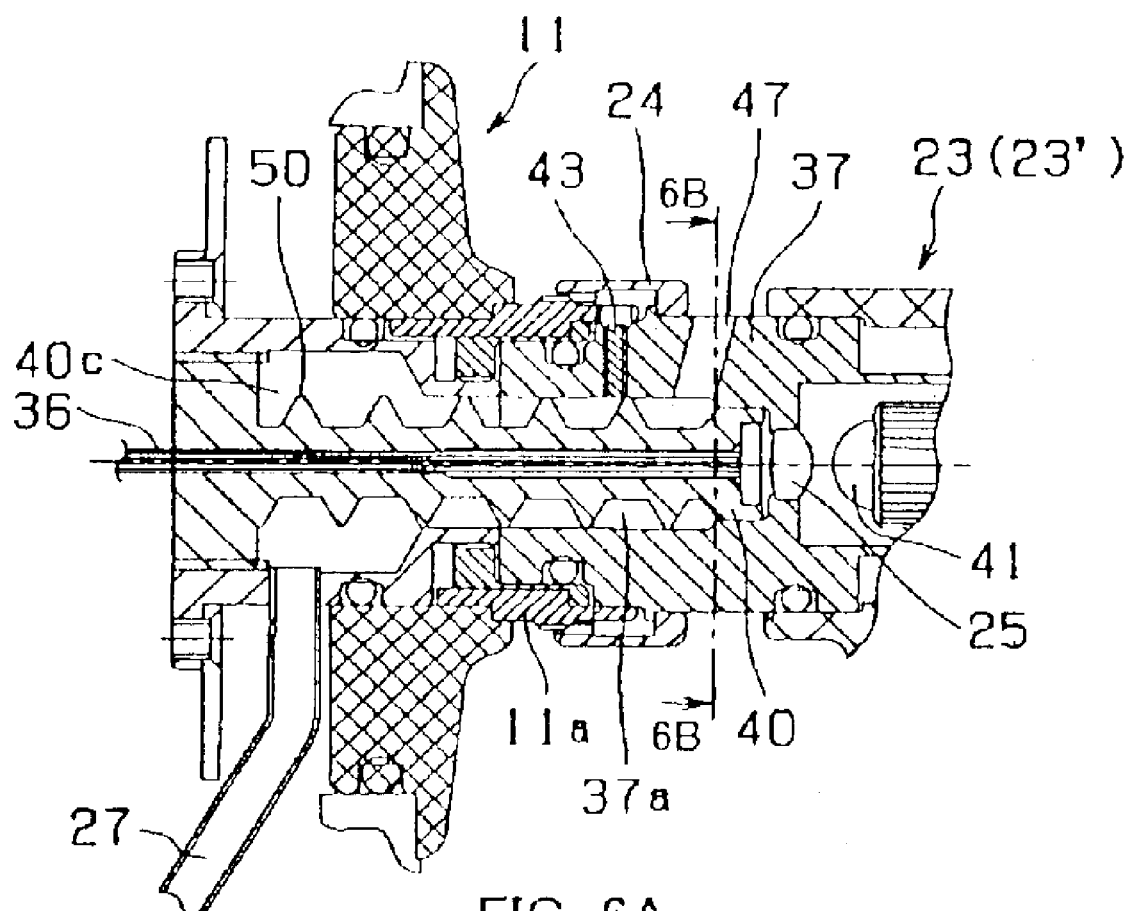
FIGS. 6A and 6B are cross-sectional views showing the construction of the light source connecting portion of the manipulating part and the construction of the light source fitting socket of the external light source in a third embodiment of the endoscope apparatus according to the present invention.
Figure 6B:
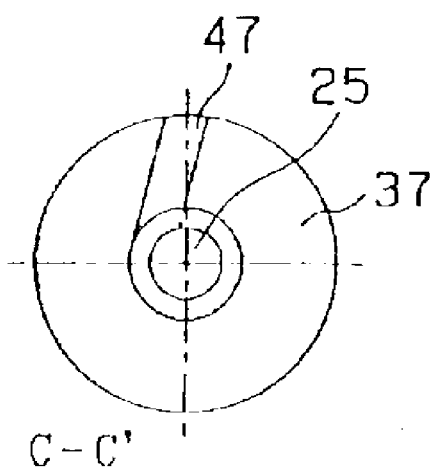

An endoscope apparatus according to a third embodiment of the invention will be described below with reference to FIGS. 6A and 6B. In the third embodiment, the endoscope-side light source connecting portion 11 and the light source socket 23 differ in construction from those of the first embodiment, and the following description refers to this point. FIG. 6A shows the state in which the endoscope-side light source connecting portion 11 and the light source socket 23 are connected to each other. In FIGS. 6A and 6B, the same reference numerals are used to denote the same parts and portions as those used in the, first embodiment, and the detailed description of the same parts and portions is omitted.

In the third embodiment, as shown in FIG. 6A, a helical fin 50 is formed around the outer circumferential portion of the fiber cable receiving member 40 provided in the endoscope-side light source connecting portion 11. In addition, the distal end of the cooling pipe 27 which communicates with the tube fitting portion 16 to which the air supply and suction device (air driving device) 100 is fitted is positioned in the space 40c surrounding the fiber cable receiving member 40 having the helical fin 50.

A communication hole 47, which causes the concave portion 37a and the outside to communicate with each other, is provided in the guide member 37 of the light source socket 23. The communication hole 47 is disposed at an angle offset from the radial direction of the central axis of the fiber cable receiving member 40, and is formed to extend in a direction slightly inclined from a direction perpendicular to the axis of the guide member 37 (refer to FIGS. 6A and 6B). The pin 43 has a construction that does not contain a hollow passage.

In this construction, because the helical fin 50 is formed around the outer circumferential portion of the fiber cable receiving member 40, the surface area of the fiber cable receiving member 40 is large, whereby heat can be transferred far more advantageously. In addition, supplied air which flows around the outer circumferential portion of the fiber cable receiving member 40 is made to flow helically owing to the helical fin 50, and flows out through the communication hole 47 of the light source socket 23. Accordingly, it is possible to increase the cooling effect.

Figure 7:
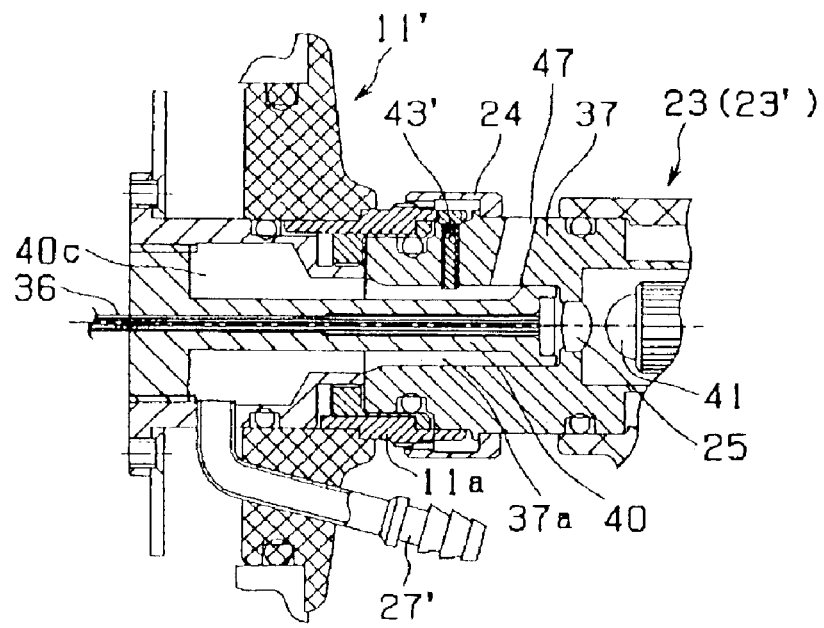
FIG. 7 is a cross-sectional view showing the construction of the light source connecting portion of the manipulating part and the construction of the light source fitting socket of the external light source in a fourth embodiment of the endoscope apparatus according to the present invention.
Figure 8:
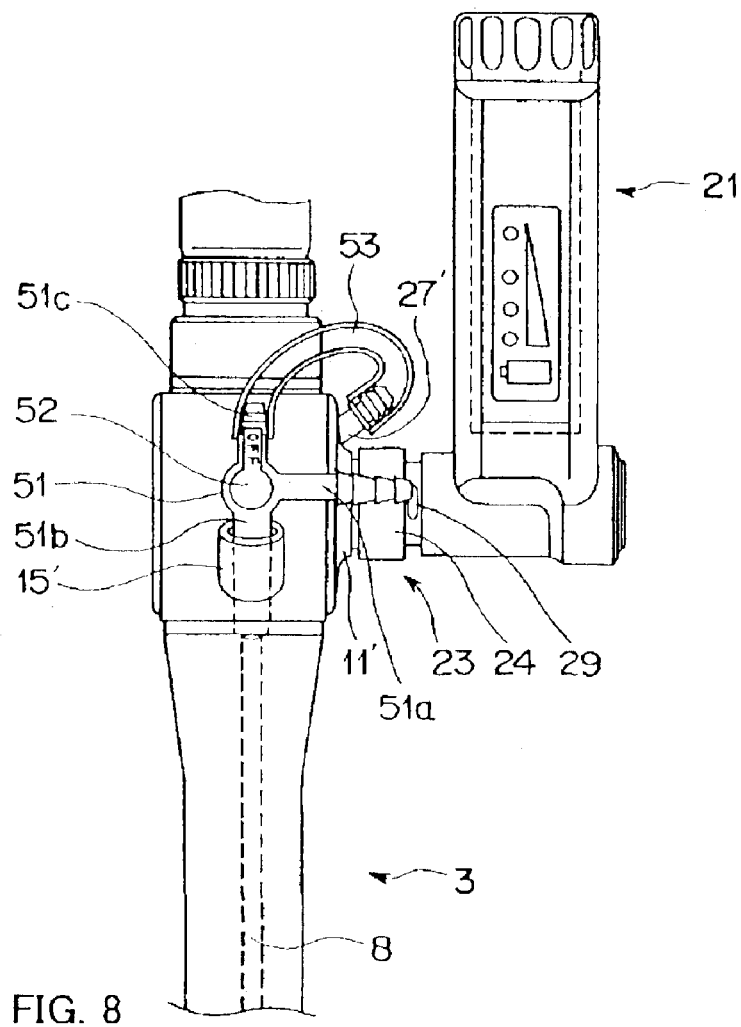
FIG. 8 is a plan view showing the state of connection between the manipulating part of the endoscope and the battery-driven light source in the fourth embodiment of the endoscope apparatus according to the present invention.

An endoscope apparatus according to a fourth embodiment of the invention will be described below with reference to FIGS. 7 and 8. In the fourth embodiment, an endoscope-side light source connecting portion 11' and the light source socket 23 differ in construction from those of the first embodiment, and the following description refers to this point. FIG. 7 shows the state in which the endoscope-side light source connecting portion 11' and the light-source socket 23 are connected to each other, and FIG. 8 shows the state in which the battery light source 21 is fitted to the manipulating part 3. In FIGS. 7 and 8, the same reference numerals are used to denote the same parts and portions as those used in the first embodiment, and the detailed description of the same parts and portions is omitted.

As shown in FIG. 7, the endoscope-side light source connecting portion 11 of the endoscope apparatus according to the fourth embodiment has a cooling pipe fitting portion 27' provided at the other end of the cooling pipe 27 which communicates with the-space 40c surrounding the fiber cable receiving member 40. The cooling pipe fitting portion 27' is positioned at the outside of the endoscope 1, and an air supply and suction tube 53 which will be described later is fitted to the cooling pipe fitting portion 27'.

Similarly to the case of the third embodiment (as shown in FIGS. 6A and 6B), the communication hole 47, which causes the concave portion 37a and the outside to communicate with each other, is provided in the guide member 37 of the light source socket 23. The communication hole 47 is disposed at an angle offset from the radial direction of the central axis of the fiber cable receiving member 40, and is formed to extend in a direction slightly inclined from a direction perpendicular to the axis of the guide member 37.

In addition, as shown in FIG. 8, a second connecting portion 51b of a three-way cock 51 having a switching lever 52 is fitted to an air supply and suction connecting portion (air connecting portion) 15' to which the proximal end of the air supply and suction channel 8 disposed to extend from the manipulating part 3 to the inserting part 2 is connected. This three-way cock 51 has a first connecting portion 51*a*, the second connecting portion 51*b* and a third connecting portion 51*c* all of which are disposed in an approximately T-like form, and also has the switching lever 52 to be manipulated to switch a plug disposed at the intersection of the first to third connecting portions 51*a* to 51*c*. The switching lever 52 has the function of closing the first connecting portion 51*a* and the function of causing the first connecting portion 51*a* to communicate with either of the second connecting portion 51*b* and the third connecting portion 51*c*.

The first connecting portion 51*a* of the three-way cock 51 is removably connected to the air supply and suction device 100. The second connecting portion 51*b* is removably connected to the air supply and suction connecting portion 15' of the manipulating part 3. One end of the air supply and suction tube 53 is removably connected to the third connecting portion 51*c*. The other end of the air supply and suction tube 53 is removably connected to the cooling pipe fitting portion 27' of the endoscope-side light source connecting portion 11'.

Namely, the air supply and suction device 100 is connected to the channel 8 by the three-way cock 51 through the air supply and suction connecting portion 15' provided in the manipulating part 3. In addition, the air supply and suction device 100 is connected to the cooling pipe fitting member 27' of the endoscope-side light source connecting portion 11' provided in the manipulating part 3, by the three-way cock 51 through the air supply and suction connecting portion 15' and the air supply and suction tube 53.

In this construction, when the switching lever 52 is set at the OFF position shown in FIG. 8, an air supply or suction force from the air supply and suction device 100 connected to the first connecting portion 51*a* of the three-way cock 51 is transmitted from the first connecting portion 51*a* to the channel 8 through the second connecting portion 51*b* and the air supply and suction connecting portion 15'. When the switching lever 52 is switched from the OFF position to the position of the first connecting portion 51*a*, an air supply or suction force from the air supply and suction device 100 connected to the first connecting portion 51*a* of the three-way cock 51 is not transmitted to either of the second connecting portion 51*b* and the third connecting portion 51*c*. When the switching lever 52 is switched from the position of the first connecting portion 51*a* to the position of the second connecting portion 51*b*, an air supply or suction force from the air supply and suction device 100 connected to the first connecting portion 51*a* of the three-way cock 51 is transmitted from the first connecting portion 51*a* to the space 40*c* surrounding the fiber cable receiving member 40 of the endoscope-side light source connecting portion 11' through the third connecting portion 51*c*, the air supply and suction tube 53 and the cooling pipe fitting member 27' of the endoscope-side light source connecting portion 11'.

In this manner, when the switching lever 52 of the three-way cock 51 is in the state of being switched to the position of the second connecting portion 51*b*, the supply or suction of air is caused around the outer circumferential portion of the fiber cable receiving member 40 of the endoscope-side light source connecting portion 11 by the air supply or suction force from the air supply and suction device 100. Accordingly, the heat of the fiber cable receiving member 40 and the light source socket 23 can be transferred to the atmosphere.

Incidentally, in the fourth embodiment, the shape and the construction of the cooling pipe fitting member 27' or the fiber cable receiving member 40 of the endoscope-side light source connecting portion 11' and the shape and the construction of the light source socket 23 can be freely designed without departing from the gist of the invention. For example, the shapes and the constructions described above in connection with the first to third embodiments can be freely combined.

In the fourth embodiment, since the three-way cock 51 can be removed from the channel 8, the air supply and suction tube 53 and the air supply and suction device 100, the three-way cock 51, the channel 8, the air supply and suction tube 53 and the like can be cleaned more fully. Furthermore, the three-way cock 51 can also be made disposable as required.

According to each of the above-described embodiments, a passage (the space 40*c*) through which flows a fluid for cooling heat generated due to light losses occurring in a connection portion is formed in the connection portion through which illuminating light from an external light source device is allowed to enter the endoscope when the illuminating light is to be introduced into the endoscope. Accordingly, the heat generated in the connection portion can be efficiently cooled. Accordingly, even when a user touches the outer periphery of the connection portion during manipulation, the user merely feels a moderate degree of heat. In addition, even in the case where the connection portion is located near a light source, the possibility decreases that the light source heats the connection portion therefore availability of a high-intensity lamp as a light source may be increased.

In each of the embodiments, air (for example, air to be supplied or sucked in the endoscope) has been introduced as a cooling fluid. However, water (water to be fed in the endoscope can be preferably used) or oxygen (medical oxygen, can be preferably used) can also be used as another preferred example of a cooling fluid.

In each of the embodiments, it has been proposed that air supplied or sucked by an air supply and suction device (an air driving device, for example, a compressor) which performs air supply or air suction through an endoscope is used as an example of the cooling fluid. This construction does not need a new device to handle the cooling fluid.

In each of the embodiments, it has been proposed to provide a structure that switches the flow passage of air from the air driving device between an air channel and a cooling passage in the endoscope. Accordingly, except during the manipulation of air supply or air suction in the endoscope by means of the air driving device connected to an air connecting portion, air supply or air suction can be constantly effected on a light source connecting portion by the air driving device and heat is removed by flowing air, whereby heat generated by the projection of illuminating light from a light source device connected to the light source connecting portion is efficiently transferred. Accordingly, the user of the endoscope may need not to worry about the power of air supply and air suction of the endoscope is decreased by bypassing air flow.

As the switching structure, not only an exclusive mechanism (the switching button 17) but also a removable three-way cock has been proposed.

In addition, it has been proposed herein that a fin structure for increasing the efficiency of heat transfer be provided in the passage through which the cooling fluid flows. This fin structure functions ads a heat sink, and has the function of restricting the flowing direction of a fluid and increasing the efficiency of heat transfer. Furthermore, it has been proposed herein that a fluid be made to flow into the passage through a plurality of inlets and flow out of the passage through a plurality of outlets, to form a rotary flow and increase the efficiency of heat transfer. Furthermore, it has been proposed herein that the flow-in and flow-out directions be made directions suited to the rotary flow.

Incidentally, the endoscope according to the invention can be used as a rigid scope as well as an elastic scope. In addition, the endoscope is not limited to medical uses, and can also be applied to industrial uses.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope apparatus comprising:
   an inserting part having a light guide passage for illuminating light and an interior air channel, the inserting part being constructed to be inserted into a target to be observed;
   a manipulating part positioned on a proximal-end side of the inserting part;
   a light source connecting portion disposed on the manipulating part for coupling the light guide passage and an external light source; and
   an air channel connecting portion disposed on the manipulating part for coupling the air channel to an external air driving device;
   wherein the external air driving device is placed at least selectively in communication with a space inside of the light source connecting portion so that the air driven by the air driving device cools the inside of the light source connecting portion.

2. An endoscope apparatus according to claim 1, wherein the space has an interior fin.

3. An endoscope apparatus according to claim 2, wherein the fin has a heat radiating function.

4. An endoscope apparatus according to claim 2, wherein the fin restricts a flowing direction of the cooling fluid.

5. An endoscope apparatus according to claim 1, wherein the cooling fluid flows into the space in an oblique direction.

6. An endoscope apparatus according to claim 1, wherein the cooling fluid flows into the space from a plurality of passages.

7. An endoscope apparatus according to claim 1, wherein the cooling fluid flows out of the space in an oblique direction.

8. An endoscope apparatus according to claim 1, wherein a proximal end portion of the light guide passage is accommodated in a tubular member, and an outer circumference of the tubular member is exposed in the space in which the cooling fluid flows.

9. An endoscope apparatus according to claim 1, wherein the light guide passage is an optical fiber.

10. An endoscope apparatus comprising:
    an inserting part having a light guide passage for illuminating light and constructed to be inserted into a target to be observed;
    a manipulating part positioned on a proximal-end side of the inserting part; and
    a light source connecting portion disposed on the manipulating part and constructed to connect the light guide passage to an external light source, the light source connecting portion having a space through which a cooling fluid flows to cool at least the light source connecting portion;
    wherein the inserting part further has an interior air channel, the manipulating part further has an air connecting portion which causes an external air driving device to communicate with the air channel, the external air driving device is further placed in communication with the space inside the light source connecting portion and the communication between the external air driving device and the space inside the light source connecting portion is realized by a cooling pipe.

11. An endoscope apparatus according to claim 10, wherein the cooling pipe is provided between the air connecting portion and the light source connecting portion.

12. An endoscope apparatus according to claim 10 further comprising a switching mechanism for switching a portion with which the external air driving device is to communicate, between at least the air channel and the cooling pipe.

13. An endoscope apparatus according to claim 12, wherein the switching mechanism, during manipulation by a user, designates the air channel as the portion with which the external air driving device is to communicate, and when the manipulation is released, the switching mechanism designates the cooling pipe as the portion with which the external air driving device is to communicate.

14. An endoscope apparatus according to claim 13, wherein the switching mechanism is a push-button switch, the manipulation being depression of the push-button switch.

15. An endoscope apparatus according to claim 12, wherein the switching mechanism is a removable three-way cock.

16. An endoscope apparatus comprising:
    an inserting part having a light guide passage for illuminating light and constructed to be inserted into a target to be observed;
    a manipulating part positioned on a proximal-end side of the inserting part; and
    a light source connecting portion disposed on the manipulating part and constructed to connect the light guide passage to an external light source, the light source connecting portion having a space through which a cooling fluid flows to cool at least the light source connecting portion;
    wherein the space has an interior fin and the fin has a helical shape.

17. An endoscope apparatus comprising:
    an inserting part having a light guide passage for illuminating light and constructed to be inserted into a target to be observed;
    a manipulating part positioned on a proximal-end side of the inserting part; and
    a light source connecting portion disposed on the manipulating part and constructed to connect the light guide passage to an external light source, the light source connecting portion having a space through which a cooling fluid flows to cool at least the light source connecting portion;
    wherein the cooling fluid flows out of the space through a plurality of passages.

18. An endoscope apparatus comprising:
    an inserting part constructed to be inserted into an area to be observed, the inserting part containing at least an air channel and an illuminating fiber cable;

an air connecting portion connecting an air driving device to the air channel;

a light source connecting portion connecting an illuminating light source to the illuminating fiber cable;

a bifurcated pipe provided in the air connecting portion, one branch of the bifurcated pipe communicating with a proximal end of the air channel, and another branch of the bifurcated pipe communicating with the atmosphere through a inside of the light source connecting portion; and a switching mechanism for switching the bifurcated pipe to select either the one branch to a communicative state and the other branch to a non-communicative state.

19. An endoscope apparatus according to claim 18, wherein the one branch of the bifurcated pipe that communicates with the atmosphere through the inside of the light source connecting portion has, a cooling pipe extending from the air connecting portion and communicating with a proximal end of the light source connecting portion, a passage formed around a fiber cable receiving member which holds a proximal end portion of the illuminating fiber cable, the passage is formed by the connection between the light source connecting portion and a light source socket of the illuminating light source, and a path formed to communicate with the passage and cause an interior and exterior of the light source socket to communicate with each other.

20. An endoscope apparatus according to claim 19, wherein the cooling pipe and the path are not parallel.

21. An endoscope apparatus comprising:

an inserting part constructed to be inserted into an area to be observed, the inserting part containing at least an observing channel, an air channel and an illuminating fiber cable;

a bendable portion disposed at a distal end of the inserting part;

an air connecting portion connected to the air channel;

a light source connecting portion connected to the illuminating fiber cable;

a first connecting port to be connected to an air driving device;

a second connecting port to be connected to the air connecting portion;

a third connecting port to be connected to one end of a cooling tube;

a branched cock comprising the first connecting port and the second connecting port and the third connecting port, capable of selectively connecting the first connecting port to either one of the second connecting port and the third connecting port;

a fiber cable receiving member comprised in the light source connecting portion, holding a proximal end of the illuminating fiber cable;

a cooling pipe connecting port which communicates with a space surrounding the fiber cable receiving member, the cooling pipe connecting portion is connected to another end of the cooling tube; and a light source socket member which has a path to make the space portion surrounding the illuminating fiber cable receiving member and the atmosphere communicative, the light source socket member is to be engaged with the light source connecting portion for connecting a light source to the light source connecting portion thus the projection of illuminating light onto an end portion of the illuminating fiber cable receiving member becomes possible, wherein in a case where at least either one of manipulations for air supply and air suction is to be performed by using the air channel of the endoscope apparatus, the first connecting port of the branched cock being connected to the second connecting port, and in other cases, the first connecting port of the branched cock being connected to the third connecting port to cause air to flow into the atmosphere through the light source connecting portion and the light source socket member by means of the air driving device.

22. An endoscope apparatus comprising:

a manipulating part having a mechanism for bending and manipulating a tip portion of the endoscope apparatus;

a light source connecting portion which is positioned in the manipulating part and to which at least either one of a light guide cable for guiding illuminating light from a light source device and a battery-type light source containing a power source and a light source lamp, is to be removably connected;

an air connecting portion which is positioned in the manipulating part and to which an air tube for performing at least either one of air supply and air suction through an air channel provided on an interior of the endoscope is to be connected; and a manipulating element positioned in the manipulating part, a three way channel having three branch channels, one branch channel being connected to the air tube, another branch channel being connected to an air passage which is open to the atmosphere through an inside of the light source connecting portion, and a remaining branch channel being connected to the air channel of the endoscope, communication between the air tube and the air channel of the endoscope and communication between the air tube and the inside of the light connecting portion being selected through operation of the manipulating element.

23. An endoscope apparatus according to claim 22, wherein the passage open to the atmosphere includes a space formed when the light source connecting portion of the endoscope apparatus is connected to either one of the light guide cable and the battery-type light source.

24. An endoscope apparatus according to claim 23, wherein a plurality of air supply and suction ports are led to the space and are respectively secured at angles so that the angles do not coincide with a radial direction of an optical axis of the connecting portion.

25. An endoscope apparatus according to claim 22, wherein a fin is formed in the inside of the light source connecting portion.

26. An endoscope apparatus according to claim 22, wherein the manipulating element and the passage led to the inside of the connecting portion are removably secured to the endoscope apparatus.

27. An endoscope apparatus comprising:

an inserting part having in its inside a light guide passage for illuminating light and an air channel and constructed to be inserted into a target to be observed;

a manipulating part positioned on a proximal-end side of the inserting part;

a connector for coupling the light guide passage and an external light source provided for generating illuminating light; and a mechanism causing an external air driving device to selectively communicate with an interior of the connector and the air channel.

28. A method of cooling heat generated due to the light loss caused between an entrance of illuminating light into an endoscope and an exit of the illuminating light from an external light source, the method comprising:

introducing illuminating light into the endoscope from the external light source;

flowing a fluid through a channel provided in the endoscope; and switching at least a portion of the fluid flow from the channel to a coupling portion between the endoscope and the external light source.

* * * * *